United States Patent
Lang et al.

(10) Patent No.: US 9,888,576 B2
(45) Date of Patent: Feb. 6, 2018

(54) METHOD FOR WORKING AN APPARATUS HAVING AT LEAST ONE ELECTRICAL LAYER STRUCTURE, AND COMPONENT ARRANGEMENT FOR WORKING AN APPARATUS HAVING AT LEAST ONE ELECTRICAL LAYER STRUCTURE

(71) Applicant: OSRAM OLED GmbH, Regensburg (DE)

(72) Inventors: Erwin Lang, Regensburg (DE); Philipp Schwamb, Regensburg (DE)

(73) Assignee: OSRAM OLED GmbH, Regensburg (DE)

( * ) Notice: Subject to any disclaimer, the term of this patent is extended or adjusted under 35 U.S.C. 154(b) by 505 days.

(21) Appl. No.: 14/431,846

(22) PCT Filed: Sep. 26, 2013

(86) PCT No.: PCT/EP2013/070049
§ 371 (c)(1),
(2) Date: Mar. 27, 2015

(87) PCT Pub. No.: WO2014/049043
PCT Pub. Date: Apr. 3, 2014

(65) Prior Publication Data
US 2015/0257272 A1    Sep. 10, 2015

(30) Foreign Application Priority Data

Sep. 28, 2012   (DE) .................. 10 2012 109 208

(51) Int. Cl.
*H05K 1/18* (2006.01)
*H01L 51/52* (2006.01)
(Continued)

(52) U.S. Cl.
CPC ............ *H05K 1/18* (2013.01); *G01N 27/045* (2013.01); *H01L 51/5203* (2013.01);
(Continued)

(58) Field of Classification Search
CPC ..................................................... H05K 1/18
See application file for complete search history.

(56) References Cited

U.S. PATENT DOCUMENTS

2004/0099305 A1   5/2004   Heller
2008/0143250 A1   6/2008   Blochwitz-Nimoth et al.
2010/0187583 A1*  7/2010   Wrazien ................ B82Y 10/00
                                                    257/295

FOREIGN PATENT DOCUMENTS

DE        10344224 A1    7/2004
DE    102008016694 A1   10/2009
(Continued)

OTHER PUBLICATIONS

International Search Report based on application No. PCT/EP2013/070049 (5 pages and 3 pages of English translation) dated May 8, 2014 (Reference Purpose Only).
(Continued)

*Primary Examiner* — Jeffrey Shin
(74) *Attorney, Agent, or Firm* — Viering, Jentschura & Partner mbB (57) ABSTRACT

Various embodiments may relate to a method for working an apparatus having at least one electrical layer structure. The electrical layer structure includes a dielectric layer in physical contact with an electrically conductive layer and the electrical layer structure has a first electrical conductivity. The method may include forming an electrical connection to the dielectric layer of the electrical layer structure, and forming an electrical voltage profile at the electrical connection in such a way that a second electrical conductivity is formed; wherein the second electrical conductivity is
(Continued)

greater than the first electrical conductivity. The electrical layer structure has the second electrical conductivity after the reduction of the electrical voltage profile.

18 Claims, 5 Drawing Sheets

(51) Int. Cl.
*G01N 27/04* (2006.01)
*H05K 3/00* (2006.01)
*H05K 3/32* (2006.01)

(52) U.S. Cl.
CPC ............ *H05K 3/0044* (2013.01); *H05K 3/32* (2013.01); *H01L 2251/303* (2013.01); *Y10T 29/4913* (2015.01); *Y10T 29/49124* (2015.01)

(56) References Cited

FOREIGN PATENT DOCUMENTS

| DE | 102006059509 B4 | 5/2012 |
| EP | 1182460 A2 | 2/2002 |
| JP | 2006334766 A | 12/2006 |
| WO | 2011007296 A1 | 1/2011 |

OTHER PUBLICATIONS

Kataoka K et al: "Low contact-force and compliant MEMS probe card utilizing fritting contact", Proceedings of the IEEE 15th. Annual International Conference on Micro Electro Mechanical Systems. MEMS 2002. Las Vegas, NV, Jan. 20-24, 2002; p. 364-367, New York.

German Search Report based on Application No. 10 2012 109 208.7(5 Pages) dated Aug. 1, 2013 (Reference Purpose Only).

German Office Action based on application No. 10 2012 109 208.7 (8 pages) dated Oct. 16, 2017 (for reference purpose only).

K. Kamada et al.: Metal plating via electrochemical reduction of oxide layers formed by electrophoretic deposition; Journal of the Ceramic Society of Japan 117; 2009; pp. 926-928.

\* cited by examiner

| Sample | Beforehand [ohms] | Afterward [ohms] |
|---|---|---|
| 1 | 19 | 9.00 |
| 2 | 18 | 12.00 |
| 3 | 17 | 11.00 |
| 4 | 18 | 12.00 |
| Mean value | 18.00 | 11.00 |
| Standard deviation | 0.82 | 1.41 |

| Sample | Beforehand [ohms] | Afterward [ohms] |
|---|---|---|
| 1 | 7 | 6.4 |
| 2 | 6.9 | 6.6 |
| 3 | 6.5 | 6.4 |
| 4 | 57 | 7.2 |
| 5 | 32 | 7.6 |
| 6 | 16 | 8.4 |
| 7 | 9 | 8.3 |
| 8 | 8.4 | 7.3 |
| Mean value | 17.85 | 7.28 |
| Standard deviation | 18.01 | 0.79 |

| Sample | Beforehand [ohms] | Afterward [ohms] |
|---|---|---|
| 1 | 20.00 | 0.4 |
| 2 | 51.00 | 0.3 |
| 3 | 12.00 | 0.4 |
| 4 | 50.00 | 0.3 |
| 5 | 100.00 | 0.7 |
| 6 | 5.80 | 0.8 |
| 7 | 5.80 | 0.6 |
| 8 | 40.00 | 0.6 |
| Mean value | 35.58 | 0.51 |
| Standard deviation | 32.04 | 0.19 |

METHOD FOR WORKING AN APPARATUS HAVING AT LEAST ONE ELECTRICAL LAYER STRUCTURE, AND COMPONENT ARRANGEMENT FOR WORKING AN APPARATUS HAVING AT LEAST ONE ELECTRICAL LAYER STRUCTURE

RELATED APPLICATIONS

The present application is a national stage entry according to 35 U.S.C. § 371 of PCT application No.: PCT/EP2013/070049 filed on Sep. 26, 2013, which claims priority from German application No.: 10 2012 109 208.7 filed on Sep. 28, 2012, and is incorporated herein by reference in its entirety.

TECHNICAL FIELD

In various embodiments, a method for working an apparatus having at least one electrical layer structure and a component arrangement for working an apparatus having at least one electrical layer structure are provided.

BACKGROUND

During the production of electrical components, for example electronic components, for example an optoelectronic component, for example an organic optoelectronic component, for example organic light emitting diodes (OLED), oxidation of electrically conductive layers can occur. The latter can thereby become electrically nonconductive or at least reduced in terms of their conductivity, for example oxidation of parts of a metal layer to form a dielectric metal oxide layer.

In the application of the electrical component, i.e. after electrical contact has been made with the electrically conductive layer, the dielectric oxide layer in the current path of the electrically conductive layer should, however, be electrically conductive in accordance with the application. In this case, the dielectric oxide layer can form a contact resistance and lead to a voltage drop and/or conversion of electrical energy into heat, that is to say lead to an energy loss.

In one conventional method, the oxidation of electrically conductive layers during the production of electrical components is prevented by complex process measures. By way of example, the processing, that is to say the production, of the electrical components can be carried out in an uninterrupted manner in an inert gas atmosphere or under a vacuum.

SUMMARY

In various embodiments, a method for working an apparatus having at least one electrical layer structure and a component arrangement for working an apparatus having at least one electrical layer structure are provided which make it possible to produce electrical components by alternative production processes and/or simplified process conditions.

In the context of this description, an organic substance can be understood to mean a carbon compound which, regardless of the respective state of matter, is present in chemically uniform form and is characterized by characteristic physical and chemical properties. Furthermore, in the context of this description, an inorganic substance can be understood to mean a compound which, regardless of the respective state of matter, is present in chemically uniform form and is characterized by characteristic physical and chemical properties, without carbon or a simple carbon compound. In the context of this description, an organic-inorganic substance (hybrid substance) can be understood to mean a compound which, regardless of the respective state of matter, is present in chemically uniform form and is characterized by characteristic physical and chemical properties, including compound portions which contain carbon and are free of carbon. In the context of this description, the term "substance" encompasses all abovementioned substances, for example an organic substance, an inorganic substance, and/or a hybrid substance. Furthermore, in the context of this description, a substance mixture can be understood to mean something which has constituents consisting of two or more different substances, the constituents of which are very finely dispersed, for example. A substance class should be understood to mean a substance or a substance mixture including one or more organic substance(s), one or more inorganic substance(s) or one or more hybrid substance(s). The term "material" can be used synonymously with the term "substance".

A substance or substance mixture which includes or is formed from an oxide can be an electrical insulator, i.e. can be dielectric, for example aluminum oxide; or can be electrically conductive or semiconducting, for example zinc oxide, indium tin oxide.

A close connection of a first body to a second body can be positively locking, force-locking and/or cohesive. The connections can be embodied as releasable, i.e. reversible, for example a screw connection, a hook and loop fastener. However, the connections can also be embodied as non-releasable, i.e. irreversible, for example a riveted connection, an adhesively bonded connection. In this case, a non-releasable connection can be separated only by the connection means being destroyed.

In the case of a positively locking connection, the movement of the first body can be restricted by a surface of the second body, wherein the first body moves perpendicularly, i.e. normally, in the direction of the restricting surface of the second body. A pin (first body) in a blind hole (second body) can be restricted in movement for example in five of the six spatial directions.

In the case of a force-locking connection, on account of a physical contact of the two bodies under pressure, a static friction can restrict a movement of the first body parallel to the second body. One example of a force-locking connection may be, for example, a bottle cork in a bottle neck or a dowel with an interference fit in a corresponding dowel hole. Furthermore, the force-locking connection can be formed by a press fit between a first body and a second body. By way of example, a diameter of the holding pin can be chosen such that it can still just be inserted into the holding cutout with deformation of the holding pin and/or of the corresponding holding cutout, but can be removed again from the latter only with increased expenditure of force.

In the case of a cohesive connection, the first body can be connected to the second body by atomic and/or molecular forces. Cohesive connections can often be non-releasable connections.

In the context of this description, an electrical component can be understood to mean a component which can form a current of charged elementary particles by an electrical potential difference. In this case, an electrical potential difference can be understood illustratively as an imbalance in the number of differently charged elementary particles.

In the context of this description, an electronic component can be understood to mean a component which concerns the control, regulation or amplification of an electric current, for example by the use of semiconductor components. An electronic component may include a component from the group of the following components: for example a diode, a transistor, a thermogenerator, an integrated circuits, a thyristor.

In the context of this description, an optoelectronic component can be understood to mean an embodiment of an electronic component, wherein the optoelectronic component includes an optically active region. The optically active region can absorb electromagnetic radiation and form a photocurrent therefrom or can emit electromagnetic radiation by a voltage applied to the optically active region.

In various embodiments, a component which emits/absorbs electromagnetic radiation can be a semiconductor component which emits/absorbs electromagnetic radiation, and/or can be embodied as a diode which emits/absorbs electromagnetic radiation, as an organic diode which emits/absorbs electromagnetic radiation, as a transistor which emits/absorbs electromagnetic radiation or as an organic transistor which emits/absorbs electromagnetic radiation.

The electromagnetic radiation can be light in the visible range, UV radiation and/or infrared radiation, for example. In this connection, the component which emits electromagnetic radiation can be embodied for example as a light emitting diode (LED), as an organic light emitting diode (OLED), as a transistor which emits electromagnetic radiation or as an organic transistor which emits electromagnetic radiation. In various embodiments, the component which emits electromagnetic radiation can be part of an integrated circuit. Furthermore, a plurality of components which emit electromagnetic radiation can be provided, for example in a manner accommodated in a common housing.

In this connection, the component which absorbs electromagnetic radiation can be embodied for example as a diode or transistor which absorbs electromagnetic radiation, for example a photodiode or a solar cell. In various embodiments, the component which absorbs electromagnetic radiation can be part of an integrated circuit. Furthermore, a plurality of components which absorb electromagnetic radiation can be provided, for example in a manner accommodated in a common housing.

In the context of this description, providing electromagnetic radiation can be understood to mean emitting electromagnetic radiation.

In the context of this description, taking up electromagnetic radiation can be understood to mean absorbing electromagnetic radiation.

In the context of this description, an optoelectronic component can be embodied as an organic optoelectronic component or an inorganic optoelectronic component.

An organic optoelectronic component may include in the optically active region an organic, electrically conductive substance or an organic, electrically conductive substance mixture, for example an optically active, organic substance or an optically active, organic substance mixture.

In the context of this description, an inorganic optoelectronic component which provides electromagnetic radiation can be designed as a wired light emitting diode, a surface mounted light emitting diode (surface mounted device—SMD) or a chip-on-board light emitting diode (die).

In the context of this description, an inorganic semiconductor chip which can provide electromagnetic radiation can be understood as an LED chip.

An inorganic optoelectronic component may include for example a semiconductor chip which provides electromagnetic radiation (wired LED, SMD) or can be designed as a semiconductor chip which provides electromagnetic radiation (chip-on-board).

A package or a housing can be applied and/or formed on or above the semiconductor chip.

The package can be formed for example as an encapsulation, optical lens and/or as a converter element.

A wired light emitting diode may include a semiconductor chip which can provide electromagnetic radiation, for example an LED chip. The semiconductor chip can be encapsulated for example with a plastic cap.

The plastic cap can protect the LED chip against external, harmful influences, for example oxygen and/or water, during manufacture and during operation.

A surface mounted light emitting diode (SMD) may include an LED chip in a housing. The housing can be closely fixed to a substrate.

A chip-on-board light emitting diode may include an LED chip fixed on a substrate, wherein the LED chip can have neither a housing nor contact pads.

The individual LED chips can be applied or formed for example on a substrate, for example a printed circuit board.

The LED chips can be wired to the printed circuit board by contact pads (wire bonding). The wirings can be effected by gold wires, for example.

In various embodiments, a method for working an apparatus having at least one electrical layer structure is provided, wherein the electrical layer structure includes a dielectric layer in physical contact with an electrically conductive layer and the electrical layer structure has a first electrical conductivity, the method including: forming an electrical connection to the dielectric layer of the electrical layer structure; forming an electrical voltage profile at the electrical connection in such a way that a second electrical conductivity is formed; wherein the second electrical conductivity is greater than the first electrical conductivity; and wherein the electrical layer structure has the second electrical conductivity after the reduction of the electrical voltage profile.

In one configuration of the method, the applied electrical voltage profile can have a maximum magnitude of the voltage which is greater than the breakdown voltage of the substance or of the substance mixture of the dielectric layer.

As a result, for example, an electrical breakdown of the dielectric layer can occur, as a result of which at least one electrically conductive path is formed in the dielectric layer. The electrically conductive path can be formed by removing of the dielectric substance or substance mixture from the current path. The removal may include migration, conversion and/or evaporation of the dielectric substance or substance mixture.

In one configuration of the method, the second electrical conductivity can be greater than the first electrical conductivity, for example by virtue of the contact resistance of the electrical layer structure being lower by at least a factor of approximately 2 or more with respect to the contact resistance of the electrically conductive structure before the method.

In one configuration of the method, the apparatus may include an electronic component unit, wherein the electrical layer structure is formed as a region of the electronic component unit or is electrically connected to a region of the electronic component unit.

In one configuration of the method, the electrically conductive layer of the electrical layer structure can be designed as an electrical bus which is electrically connected to the electronic component unit, for example as a busbar.

In one configuration of the method, the electrically conductive layer of the electrical layer structure can be designed as an electrode or a contact pad of the electronic component unit.

In one configuration of the method, the dielectric layer of the electrical layer structure may be designed as a thin-film encapsulation and/or include a dielectric metal oxide.

In one configuration of the method, the electrically conductive layer of the electrical layer structure can be embodied for example as a metal layer.

In one configuration of the method, the electrically conductive layer may include or be formed from one of the following substances: copper, silver, gold, platinum, aluminum, zinc, zirconium, titanium, silicon, indium and mixtures and alloys thereof.

In one configuration of the method, the electrically conductive layer of the electrical layer structure can have for example a thickness in a range of approximately 100 nm to approximately 2 mm, for example in a range of approximately 200 nm to approximately 50 µm.

In one configuration of the method, the dielectric layer may include an oxide compound of the substance or of the substance mixture of the electrically conductive layer, for example can be designed as a native oxide layer.

In one configuration of the method, the dielectric layer may include or be formed from one of the following substances: aluminum oxide, zinc oxide, zirconium oxide, titanium oxide, hafnium oxide, tantalum oxide, lanthanum oxide, silicon oxide, silicon nitride, silicon oxynitride, tin oxide, copper oxide, chromium oxide, silver oxide, molybdenum oxide, tungsten oxide, vanadium oxide, magnesium oxide and mixtures and alloys thereof.

In one configuration of the method, the dielectric layer of the electrical layer structure can have for example a thickness in a range of approximately 0.1 nm to approximately 2 mm, for example in a range of approximately 2 nm to approximately 500 nm.

In one configuration of the method, the electrical connection can be formed in a close fashion, for example in a cohesive fashion.

In one configuration of the method, the electrical connection can be designed to be temporary and/or reversible.

A temporary and reversible electrical connection can be realized for example as forming physical contact between contact pins and the electrical layer structure, for example contacting the surface of the electrical layer structure with contact pins of a voltage source.

A contact pin can also be designated as a pin.

In one configuration of the method, the electrical connection can be designed in such a way that the electrical circuit of the electrical connection is closed by the electrical layer structure.

In one configuration of the method, the magnitude of the voltage of the electrical voltage profile can be temporally modulated.

In one configuration of the method, the electrical voltage profile can have one of the following temporal modulations: sinusoidal, cosinusoidal, sawtooth-shaped, triangular, rectangular, pulsed.

An electrical voltage pulse can have for example one of the following voltage profiles: Gauβ, Lorentz, Voigt, Gumbel, Laplace, Levy, Rayleigh, Rossi, Student t-profile or the like.

In one configuration of the method, an electrical voltage pulse can have a half-life and/or a pulse duration in a range of approximately 1 µs to approximately 5 s.

In one configuration of the method, the voltage profile can have an individual voltage pulse or a frequency in a range of approximately 0.2 Hz to approximately 1 MHz.

In one configuration of the method, the temporal modulation may include a pulse width modulation.

In one configuration of the method, the maximum magnitude of the electrical voltage profile can have a magnitude of greater than approximately 1 V, for example in a range of approximately 1 V to 100 V. In the case of native oxide layers as dielectric layer, for example, a magnitude of greater than approximately 1 V can suffice for making contact through the dielectric layer. A magnitude of very much greater than 1 V, for example in a range of approximately 30 V to several kV, can be necessary for example when making contact through dielectric layers having a larger layer thickness, for example greater than approximately 20 nm, for example in a range of approximately 100 nm to approximately 100 µm.

The maximum magnitude of the electrical voltage profile can also be designated as peak voltage and/or voltage amplitude, wherein the maximum magnitude of the electrical voltage profile can be temporally modulated.

In one configuration of the method, the temporal modulation of the voltage profile can be correlated and/or coupled with the electrical conductivity, for example by virtue of the electrical conductivity of the apparatus being measured after a voltage pulse.

In one configuration of the method, the peak voltage of a voltage pulse and/or the number of pulses can be a function of the electrical conductivity of the apparatus, for example of the thickness of the non-removed dielectric layer in the current path.

The concrete magnitude of the electrical voltage can be dependent on the thickness of the dielectric layer and the dielectric properties of the substance or of the substance mixture of the dielectric layer. However, the dielectric layer should have a maximum thickness, such that the maximum magnitude of the voltage is maximally of a value such that further layers which are in electrical contact with the electrical layer structure are not damaged by the voltage.

In one configuration of the method, in at least one region of the electrical layer structure a part of the dielectric layer of the electrical layer structure can be removed before the electrical connection is formed.

In one configuration of the method, the removal of a part of the dielectric layer can be effected in such a way that another part of the dielectric layer remains on or above the electrically conductive layer.

The removal of a part of the dielectric layer can reduce the magnitude of the minimum voltage for the electrical breakdown of the dielectric layer.

In addition, the electrical breakdown of the dielectric layer in physical contact with the electrically conductive layer, with regard to ballistic exposure of the electrically conductive layer, can form a lower surface roughness of the electrically conductive layer.

In one configuration of the method, removing a part of the dielectric layer may include ballistically removing the dielectric layer.

In other words: a part of the dielectric layer can be exposed ballistically.

Ballistically exposing the regions to be exposed can be realized for example by bombardment of the region to be exposed with particles, molecules, atoms, ions, electrons and/or photons, for example laser ablation.

In one configuration of the method, removing a part of the dielectric layer may include laser ablation.

Laser ablation can be embodied for example with a laser having a wavelength in a range of approximately 200 nm to approximately 1700 nm, for example in a focused manner, for example with a focus diameter in a range of approximately 10 μm to approximately 2000 μm, for example in a pulsed manner, for example with a pulse duration in a range of approximately 100 fs to approximately 0.5 ms, for example with a power of approximately 50 mW to approximately 1000 mW, for example with a power density of approximately 100 kW/cm$^2$ to approximately 10 GW/cm$^2$, and for example with a repetition rate in a range of approximately 0.2 Hz to approximately 1000 Hz.

In one configuration of the method, working the apparatus in accordance with various configurations can be embodied as a step for removing a thin-film encapsulation on or above an electrode or a contact pad, for example as a step for exposing contact pads, for example after laser ablation of a thin-film encapsulation on or above the contact pads.

In one configuration of the method, the electrical connection to the electrical layer structure can be formed in the region of the removed dielectric layer.

In one configuration of the method, the dielectric layer can be at least partly removed from at least two regions of the electrical layer structure.

In one configuration of the method, the electrical connection can be formed in such a way that the electrical voltage profile is formed over the at least two regions of the electrical layer structure from which the dielectric layer was at least partly removed.

In other words: the electrical layer structure can be self-contacted in accordance with various configurations, wherein the dielectric layer acts as an electrical resistor and the electrically conductive layer acts as an electrical conductor.

In one configuration of the method, the apparatus can be formed as a component which provides electromagnetic radiation, for example as a light emitting diode, for example an organic light emitting diode.

In one configuration of the method, the apparatus can be formed as a component which takes up electromagnetic radiation, for example a solar cell, for example an organic solar cell.

In one configuration of the method, the apparatus can be embodied as an optoelectronic component having copper contacts.

In one configuration of the method, the electrical layer structure can be designed as a copper contact track, for example of a radio transponder (RFID chip—radio-frequency identification) and/or in components having printed copper inks.

In various embodiments, a component arrangement for working an apparatus having at least one electrical layer structure having a first electrical conductivity is provided, the component arrangement including: an apparatus having at least one electrical layer structure, wherein the electrical layer structure includes a dielectric layer in physical contact with an electrically conductive layer and the electrical layer structure has a first electrical conductivity; a voltage source designed for providing a modulatable voltage profile, wherein the voltage source is electrically connected to the electrical layer structure in such a way that the electrical circuit is closed by the electrical layer structure; a control unit designed for controlling the voltage profile of the voltage source; a measuring device for measuring the electrical conductivity of the electrical layer structure, wherein the measuring device is designed in such a way that the measured electrical conductivity is communicated to the control unit; wherein the control unit is designed in such a way that the voltage profile is controlled depending on the measured electrical conductivity.

In one configuration of the component arrangement, the voltage source can be designed for providing a constant DC current, for example have a rectifier for an electric input current.

In one configuration of the component arrangement, the measuring device can be designed for measuring the electrical resistance of the electrical layer structure, for example as a resistance bridge, for example a Wheatstone bridge.

In one configuration of the component arrangement, the measuring device can be designed for measuring the electrical voltage drop across the electrical layer structure, for example as a digital voltmeter.

In one configuration of the component arrangement, the measuring device can be designed for measuring the electric current through the electrical layer structure, for example as a digital ammeter.

In one configuration of the component arrangement, the control unit can be designed as a phase dimmer, wherein the control signal for phase chopping control or phase gating control is a function of the measured conductivity of the electrical layer structure.

In one configuration of the component arrangement, the control unit can be designed as a pulse modulator, for example for pulse width modulation or pulse frequency modulation, wherein the control signal for pulse modulation is a function of the measured conductivity of the electrical layer structure.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the disclosed embodiments. In the following description, various embodiments described with reference to the following drawings, in which.

DETAILED DESCRIPTION

In the following detailed description, reference is made to the accompanying drawings, which form part of this description and show for illustration purposes specific embodiments in which the invention can be implemented. In this regard, direction terminology such as, for instance, "at the top", "at the bottom", "at the front", "at the back", "front", "rear", etc. is used with respect to the orientation of the figure(s) described. Since component parts of embodiments can be positioned in a number of different orientations, the direction terminology serves for illustration and is not restrictive in any way whatsoever. It goes without saying that other embodiments can be used and structural or logical changes can be made, without departing from the scope of protection of the present invention. It goes without saying that the features of the various embodiments described herein can be combined with one another, unless specifically indicated otherwise. Therefore, the following detailed description should not be interpreted in a restrictive sense, and the scope of protection of the present invention is defined by the appended claims.

In the context of this description, the terms "connected" and "coupled" are used to describe both a direct and an indirect connection and a direct or indirect coupling. In the figures, identical or similar elements are provided with identical reference signs, insofar as this is expedient.

Figure 1:
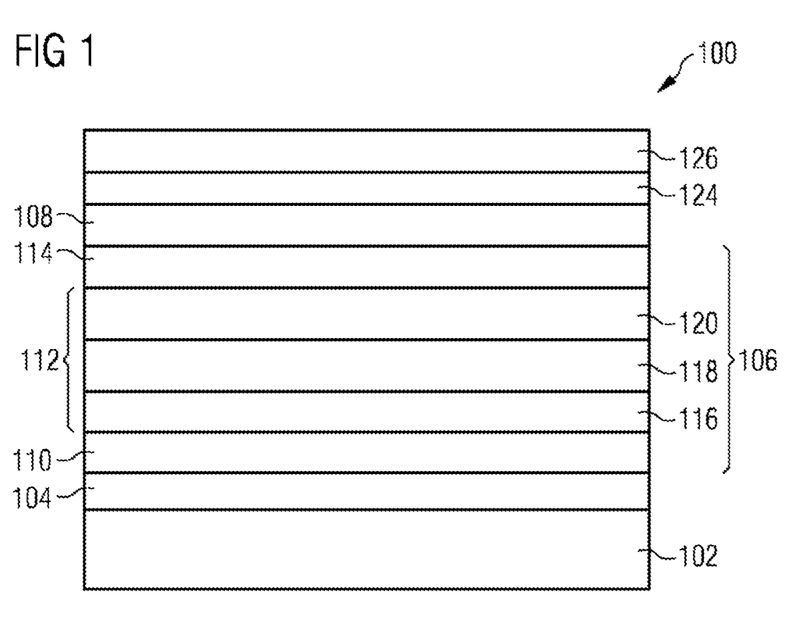
FIG. 1 shows a schematic cross-sectional view of an optoelectronic component, in accordance with various configurations.

FIG. 1 shows a schematic cross-sectional view of an optoelectronic component, in accordance with various embodiments.

The optoelectronic component 100, for example an electronic component 100 which provides electromagnetic radiation, for example a light emitting component 100, for example in the form of an organic light emitting diode 100, can have a carrier 102. The carrier 102 can serve for example as a carrier element for electronic elements or layers, for example light emitting elements. By way of example, the carrier 102 may include or be formed from glass, quartz, and/or a semiconductor material or any other suitable substance. Furthermore, the carrier 102 may include or be formed from a plastics film or a laminate including one or including a plurality of plastics films. The plastic may include or be formed from one or more polyolefins (for example high or low density polyethylene (PE) or polypropylene (PP)). Furthermore, the plastic may include or be formed from polyvinyl chloride (PVC), polystyrene (PS), polyester and/or polycarbonate (PC), polyethylene terephthalate (PET), polyethersulfone (PES) and/or polyethylene naphthalate (PEN). The carrier 102 may include one or more of the substances mentioned above. The carrier 102 may include or be formed from a metal or a metal compound, for example copper, silver, gold, platinum or the like.

A carrier 102 including a metal or a metal compound can also be embodied as a metal film or a metal-coated film.

The carrier 102 can be embodied as translucent or even transparent.

In various embodiments, the term "translucent" or "translucent layer" can be understood to mean that a layer is transmissive to light, for example to the light generated by the light emitting component, for example in one or more wavelength ranges, for example to light in a wavelength range of visible light (for example at least in a partial range of the wavelength range of from 380 nm to 780 nm). By way of example, in various embodiments, the term "translucent layer" should be understood to mean that substantially the entire quantity of light coupled into a structure (for example a layer) is also coupled out from the structure (for example layer), wherein part of the light can be scattered in this case.

In various embodiments, the term "transparent" or "transparent layer" can be understood to mean that a layer is transmissive to light (for example at least in a partial range of the wavelength range of from 380 nm to 780 nm), wherein light coupled into a structure (for example a layer) is also coupled out from the structure (for example layer) substantially without scattering or light conversion. Consequently, in various embodiments, "transparent" should be regarded as a special case of "translucent".

For the case where, for example, a light emitting monochromatic or emission spectrum-limited electronic component is intended to be provided, it suffices for the optically translucent layer structure to be translucent at least in a partial range of the wavelength range of the desired monochromatic light or for the limited emission spectrum.

In various embodiments, the organic light emitting diode 100 (or else the light emitting components in accordance with the embodiments that have been described above or will be described below) can be designed as a so-called top and bottom emitter. A top and/or bottom emitter can also be designated as an optically transparent component, for example a transparent organic light emitting diode.

In various embodiments, a barrier layer 104 can optionally be arranged on or above the carrier 102. The barrier layer 104 may include or consist of one or more of the following materials: aluminum oxide, zinc oxide, zirconium oxide, titanium oxide, hafnium oxide, tantalum oxide, lanthanum oxide, silicon oxide, silicon nitride, silicon oxynitride, indium tin oxide, indium zinc oxide, aluminum-doped zinc oxide, and mixtures and alloys thereof. Furthermore, in various embodiments, the barrier layer 104 can have a layer thickness in a range of approximately 0.1 nm (one atomic layer) to approximately 5000 nm, for example a layer thickness in a range of approximately 10 nm to approximately 200 nm, for example a layer thickness of approximately 40 nm.

An electrically active region 106 of the light emitting component 100 can be arranged on or above the barrier layer 104. The electrically active region 106 can be understood as that region of the light emitting component 100 in which an electric current for the operation of the light emitting component 100 flows. In various embodiments, the electrically active region 106 may include a first electrode 110, a second electrode 114 and an organic functional layer structure 112, as are explained in even greater detail below.

In this regard, in various embodiments, the first electrode 110 (for example in the form of a first electrode layer 110) can be applied on or above the barrier layer 104 (or, if the barrier layer 104 is not present, on or above the carrier 102). The first electrode 110 (also designated hereinafter as bottom electrode 110) can be formed from an electrically conductive substance, such as, for example, a metal or a transparent conductive oxide (TCO) or a layer stack including a plurality of layers of the same metal or different metals and/or the same TCO or different TCOs. Transparent conductive oxides are transparent conductive substances, for example metal oxides, such as, for example, zinc oxide, tin oxide, cadmium oxide, titanium oxide, indium oxide, or indium tin oxide (ITO). Alongside binary metal-oxygen compounds, such as, for example, ZnO, $SnO_2$, or $In_2O_3$, ternary metal-oxygen compounds, such as, for example, AlZnO, $Zn_2SnO_4$, $CdSnO_3$, $ZnSnO_3$, $MgIn_2O_4$, $GaInO_3$, $Zn_2In_2O_5$ or $In_4Sn_3O_{12}$, or mixtures of different transparent conductive oxides also belong to the group of TCOs and can be used in various embodiments. Furthermore, the TCOs do not necessarily correspond to a stoichiometric composition and can furthermore be p-doped or n-doped.

In various embodiments, the first electrode 110 may include a metal; for example Ag, Pt, Au, Mg, Al, Ba, In, Ca, Sm or Li, and compounds, combinations or alloys of these materials.

In various embodiments, the first electrode 110 can be formed by a layer stack of a combination of a layer of a metal on a layer of a TCO, or vice versa. One example is a silver layer applied on an indium tin oxide layer (ITO) (Ag on ITO) or ITO-Ag-ITO multilayers.

In various embodiments, the first electrode 110 may include one or a plurality of the following substances as an alternative or in addition to the abovementioned substances: networks composed of metallic nanowires and nanoparticles, for example composed of Ag; networks composed of carbon nanotubes; graphene particles and graphene layers; networks composed of semiconducting nanowires.

Furthermore, the first electrode 110 may include electrically conductive polymers or transition metal oxides or transparent electrically conductive oxides.

In various embodiments, the first electrode 110 and the carrier 102 can be formed as translucent or transparent. In the case where the first electrode 110 includes or is formed from a metal, the first electrode 110 can have for example a layer thickness of less than or equal to approximately 25 nm, for example a layer thickness of less than or equal to approximately 20 nm, for example a layer thickness of less than or equal to approximately 18 nm. Furthermore, the first electrode 110 can have for example a layer thickness of greater than or equal to approximately 10 nm, for example a layer thickness of greater than or equal to approximately 15 nm. In various embodiments, the first electrode 110 can have a layer thickness in a range of approximately 10 nm to approximately 25 nm, for example a layer thickness in a range of approximately 10 nm to approximately 18 nm, for example a layer thickness in a range of approximately 15 nm to approximately 18 nm.

Furthermore, for the case where the first electrode 110 includes or is formed from a transparent conductive oxide (TCO), the first electrode 110 can have for example a layer thickness in a range of approximately 50 nm to approximately 500 nm, for example a layer thickness in a range of approximately 75 nm to approximately 250 nm, for example a layer thickness in a range of approximately 100 nm to approximately 150 nm.

Furthermore, for the case where the first electrode 110 is formed from, for example, a network composed of metallic nanowires, for example composed of Ag, which can be combined with conductive polymers, a network composed of carbon nanotubes which can be combined with conductive polymers, or from graphene layers and composites, the first electrode 110 can have for example a layer thickness in a range of approximately 1 nm to approximately 500 nm, for example a layer thickness in a range of approximately 10 nm to approximately 400 nm, for example a layer thickness in a range of approximately 40 nm to approximately 250 nm.

The first electrode 110 can be formed as an anode, that is to say as a hole-injecting electrode, or as a cathode, that is to say as an electron-injecting electrode.

The first electrode 110 can have a first electrical contact pad, to which a first electrical potential (provided by an energy source (not illustrated), for example a current source or a voltage source) can be applied. Alternatively, the first electrical potential can be applied to the carrier 102 and then be fed indirectly to the first electrode 110 via said carrier. The first electrical potential can be, for example, the ground potential or some other predefined reference potential.

Furthermore, the electrically active region 106 of the light emitting component 100 can have an organic functional layer structure 112, which is applied or formed on or above the first electrode 110.

The organic functional layer structure 112 may include one or a plurality of emitter layers 118, for example including fluorescent and/or phosphorescent emitters, and one or a plurality of hole-conducting layers 116 (also designated as hole transport layer(s) 120). In various embodiments, one or a plurality of electron-conducting layers 116 (also designated as electron transport layer(s) 116) can alternatively or additionally be provided.

Examples of emitter materials which can be used in the light emitting component 100 in accordance with various embodiments for the emitter layer(s) 118 include organic or organometallic compounds such as derivatives of polyfluorene, polythiophene and polyphenylene (e.g. 2- or 2,5-substituted poly-p-phenylene vinylene) and metal complexes, for example iridium complexes such as blue phosphorescent FIrPic (bis(3,5-difluoro-2-(2-pyridyl)phenyl(2-carboxypyridyl) iridium III), green phosphorescent $Ir(ppy)_3$ (tris(2-phenylpyridine)iridium III), red phosphorescent Ru $(dtb-bpy)_3*2(PF_6)$ (tris[4,4'-di-tert-butyl-(2,2')-bipyridine]ruthenium(III) complex) and blue fluorescent DPAVBi (4,4-bis[4-(di-p-tolylamino)styryl]biphenyl), green fluorescent TTPA (9,10-bis[N,N-di(p-tolyl)amino]anthracene) and red fluorescent DCM2 (4-dicyanomethylene)-2-methyl-6-julolidyl-9-enyl-4H-pyran) as non-polymeric emitters. Such non-polymeric emitters can be deposited by thermal evaporation, for example. Furthermore, it is possible to use polymer emitters, which can be deposited, in particular, by a wet-chemical method such as spin coating, for example.

The emitter materials can be embedded in a matrix material in a suitable manner.

It should be pointed out that other suitable emitter materials are likewise provided in other embodiments.

The emitter materials of the emitter layer(s) 118 of the light emitting component 100 can be selected for example such that the light emitting component 100 emits white light. The emitter layer(s) 118 may include a plurality of emitter materials that emit in different colors (for example blue and yellow or blue, green and red); alternatively, the emitter layer(s) 118 can also be constructed from a plurality of partial layers, such as a blue fluorescent emitter layer 118 or blue phosphorescent emitter layer 118, a green phosphorescent emitter layer 118 and a red phosphorescent emitter layer 118. By mixing the different colors, the emission of light having a white color impression can result. Alternatively, provision can also be made for arranging a converter material in the beam path of the primary emission generated by said layers, which converter material at least partly absorbs the primary radiation and emits a secondary radiation having a different wavelength, such that a white color impression results from a (not yet white) primary radiation by virtue of the combination of primary and secondary radiation.

The organic functional layer structure 112 may generally include one or a plurality of electroluminescent layers. The one or the plurality of electroluminescent layers may include organic polymers, organic oligomers, organic monomers, organic small, non-polymeric molecules ("small molecules") or a combination of these materials. By way of example, the organic functional layer structure 112 may include one or a plurality of electroluminescent layers embodied as a hole transport layer 120, so as to enable for example in the case of an OLED an effective hole injection into an electroluminescent layer or an electroluminescent region. Alternatively, in various embodiments, the organic functional layer structure 112 may include one or a plurality of functional layers embodied as an electron transport layer 116, so as to enable for example in an OLED an effective electron injection into an electroluminescent layer or an electroluminescent region. By way of example, tertiary amines, carbazole derivatives, conductive polyaniline or polyethylene dioxythiophene can be used as material for the hole transport layer 120. In various embodiments, the one or the plurality of electroluminescent layers can be embodied as an electroluminescent layer.

In various embodiments, the hole transport layer 120 can be applied, for example deposited, on or above the first electrode 110, and the emitter layer 118 can be applied, for example deposited, on or above the hole transport layer 120. In various embodiments, the electron transport layer 116 can be applied, for example deposited, on or above the emitter layer 118.

In various embodiments, the organic functional layer structure 112 (that is to say for example the sum of the thicknesses of hole transport layer(s) 120 and emitter layer(s) 118 and electron transport layer(s) 116) can have a layer thickness of a maximum of approximately 1.5 µm, for example a layer thickness of a maximum of approximately 1.2 µm, for example a layer thickness of a maximum of approximately 1 µm, for example a layer thickness of a maximum of approximately 800 nm, for example a layer thickness of a maximum of approximately 500 nm, for example a layer thickness of a maximum of approximately 400 nm, for example a layer thickness of a maximum of approximately 300 nm. In various embodiments, the organic functional layer structure 112 can have for example a stack of a plurality of organic light emitting diodes (OLEDs) arranged directly one above another, wherein each OLED can have for example a layer thickness of a maximum of approximately 1.5 µm, for example a layer thickness of a maximum of approximately 1.2 µm, for example a layer thickness of a maximum of approximately 1 µm, for example a layer thickness of a maximum of approximately 800 nm, for example a layer thickness of a maximum of approximately 500 nm, for example a layer thickness of a maximum of approximately 400 nm, for example a layer thickness of a maximum of approximately 300 nm. In various embodiments, the organic functional layer structure 112 can have for example a stack of two, three or four OLEDs arranged directly one above another, in which case for example the organic functional layer structure 112 can have a layer thickness of a maximum of approximately 3 µm.

The light emitting component 100 may optionally generally include further organic functional layers, for example arranged on or above the one or the plurality of emitter layers 118 or on or above the electron transport layer(s) 116, which serve to further improve the functionality and thus the efficiency of the light emitting component 100.

The second electrode 114 (for example in the form of a second electrode layer 114) can be applied on or above the organic functional layer structure 112 or, if appropriate, on or above the one or the plurality of further organic functional layer structures.

In various embodiments, the second electrode 114 may include or be formed from the same substances as the first electrode 110, metals being particularly suitable in various embodiments.

In various embodiments, the second electrode 114 (for example for the case of a metallic second electrode 114) can have for example a layer thickness of less than or equal to approximately 50 nm, for example a layer thickness of less than or equal to approximately 45 nm, for example a layer thickness of less than or equal to approximately 40 nm, for example a layer thickness of less than or equal to approximately 35 nm, for example a layer thickness of less than or equal to approximately 30 nm, for example a layer thickness of less than or equal to approximately 25 nm, for example a layer thickness of less than or equal to approximately 20 nm, for example a layer thickness of less than or equal to approximately 15 nm, for example a layer thickness of less than or equal to approximately 10 nm.

The second electrode 114 can generally be formed in a similar manner to the first electrode 110, or differently than the latter. In various embodiments, the second electrode 114 can be formed from one or more of the substances and with the respective layer thickness, as described above in connection with the first electrode 110. In various embodiments, both the first electrode 110 and the second electrode 114 are formed as translucent or transparent. Consequently, the light emitting component 100 illustrated in FIG. 1 can be designed as a top and bottom emitter (to put it another way as a transparent light emitting component 100).

The second electrode 114 can be formed as an anode, that is to say as a hole-injecting electrode, or as a cathode, that is to say as an electron-injecting electrode.

The second electrode 114 can have a second electrical terminal, to which a second electrical potential (which is different than the first electrical potential), provided by the energy source, can be applied. The second electrical potential can have for example a value such that the difference with respect to the first electrical potential has a value in a range of approximately 1.5 V to approximately 20 V, for example a value in a range of approximately 2.5 V to approximately 15 V, for example a value in a range of approximately 3 V to approximately 12 V.

An encapsulation 108, for example in the form of a barrier thin-film layer/thin-film encapsulation 108, can optionally also be formed on or above the second electrode 114 and thus on or above the electrically active region 106.

In the context of this application, a "barrier thin-film layer" 108 or a "barrier thin film" 108 can be understood to mean, for example, a layer or a layer structure which is suitable for forming a barrier against chemical impurities or atmospheric substances, in particular against water (moisture) and oxygen. In other words, the barrier thin-film layer 108 is formed in such a way that OLED-damaging substances such as water, oxygen or solvent cannot penetrate through it or at most very small proportions of said substances can penetrate through it.

In accordance with one configuration, the barrier thin-film layer 108 can be formed as an individual layer (to put it another way, as a single layer). In accordance with an alternative configuration, the barrier thin-film layer 108 may include a plurality of partial layers formed one on top of another. In other words, in accordance with one configuration, the barrier thin-film layer 108 can be formed as a layer stack. The barrier thin-film layer 108 or one or a plurality of partial layers of the barrier thin-film layer 108 can be formed for example by a suitable deposition method, e.g. by an atomic layer deposition (ALD) method in accordance with one configuration, e.g. a plasma enhanced atomic layer deposition (PEALD) method or a plasmaless atomic layer deposition (PLALD) method, or by a chemical vapor deposition (CVD) method in accordance with another configuration, e.g. a plasma enhanced chemical vapor deposition (PECVD) method or a plasmaless chemical vapor deposition (PLCVD) method, or alternatively by other suitable deposition methods.

By using an atomic layer deposition (ALD) method, it is possible for very thin layers to be deposited. In particular, layers having layer thicknesses in the atomic layer range can be deposited.

In accordance with one configuration, in the case of a barrier thin-film layer 108 having a plurality of partial layers, all the partial layers can be formed by an atomic layer deposition method. A layer sequence including only ALD layers can also be designated as a "nanolaminate".

In accordance with an alternative configuration, in the case of a barrier thin-film layer 108 including a plurality of partial layers, one or a plurality of partial layers of the barrier thin-film layer 108 can be deposited by a different deposition method than an atomic layer deposition method, for example by a vapor deposition method.

In accordance with one configuration, the barrier thin-film layer 108 can have a layer thickness of approximately 0.1 nm (one atomic layer) to approximately 1000 nm, for example a layer thickness of approximately 10 nm to approximately 100 nm in accordance with one configuration, for example approximately 40 nm in accordance with one configuration.

In accordance with one configuration in which the barrier thin-film layer 108 includes a plurality of partial layers, all the partial layers can have the same layer thickness. In accordance with another configuration, the individual partial layers of the barrier thin-film layer 108 can have different layer thicknesses. In other words, at least one of the partial layers can have a different layer thickness than one or more other partial layers.

In accordance with one configuration, the barrier thin-film layer 108 or the individual partial layers of the barrier thin-film layer 108 can be formed as a translucent or transparent layer. In other words, the barrier thin-film layer 108 (or the individual partial layers of the barrier thin-film layer 108) can consist of a translucent or transparent substance (or a substance mixture that is translucent or transparent).

In accordance with one configuration, the barrier thin-film layer 108 or (in the case of a layer stack having a plurality of partial layers) one or a plurality of the partial layers of the barrier thin-film layer 108 may include or consist of one of the following substances: aluminum oxide, zinc oxide, zirconium oxide, titanium oxide, hafnium oxide, tantalum oxide, lanthanum oxide, silicon oxide, silicon nitride, silicon oxynitride, indium tin oxide, indium zinc oxide, aluminum-doped zinc oxide, and mixtures and alloys thereof. In various embodiments, the barrier thin-film layer 108 or (in the case of a layer stack having a plurality of partial layers) one or a plurality of the partial layers of the barrier thin-film layer 108 may include one or a plurality of high refractive index materials, to put it another way one or a plurality of materials having a high refractive index, for example having a refractive index of at least 2.

In one configuration, the cover 126, for example composed of glass, can be applied for example by frit bonding (glass frit bonding/glass soldering/seal glass bonding) to the barrier thin-film layer 108 by a conventional glass solder in the geometrical edge regions of the organic optoelectronic component 100.

In various embodiments, on or above the barrier thin-film layer 108, it is possible to provide an adhesive and/or a protective lacquer 124, by which, for example, a cover 126 (for example a glass cover 126, a metal film covering 126, a sealed plastics film cover 126) is fixed, for example adhesively bonded, on the barrier thin-film layer 108. In various embodiments, the optically translucent layer composed of adhesive and/or protective lacquer 124 can have a layer thickness of greater than 1 μm, for example a layer thickness of several μm. In various embodiments, the adhesive may include or be a lamination adhesive.

In various embodiments, light-scattering particles can also be embedded into the layer of the adhesive (also designated as adhesive layer), which particles can lead to a further improvement in the color angle distortion and the coupling-out efficiency. In various embodiments, the light-scattering particles provided can be dielectric scattering particles, for example, such as metal oxides, for example, such as e.g. silicon oxide ($SiO_2$), zinc oxide (ZnO), zirconium oxide ($ZrO_2$), indium tin oxide (ITO) or indium zinc oxide (IZO), gallium oxide ($Ga_2Oa$), aluminum oxide, or titanium oxide. Other particles may also be suitable provided that they have a refractive index that is different than the effective refractive index of the matrix of the translucent layer structure, for example air bubbles, acrylate, or hollow glass beads. Furthermore, by way of example, metallic nanoparticles, metals such as gold, silver, iron nanoparticles, or the like can be provided as light-scattering particles.

In various embodiments, between the second electrode 114 and the layer composed of adhesive and/or protective lacquer 124, an electrically insulating layer (not shown) can also be applied, for example SiN, for example having a layer thickness in a range of approximately 300 nm to approximately 1.5 μm, for example having a layer thickness in a range of approximately 500 nm to approximately 1 μm, in order to protect electrically unstable materials, during a wet-chemical process for example.

In various embodiments, the adhesive can be designed in such a way that it itself has a refractive index which is less than the refractive index of the cover 126. Such an adhesive can be for example a low refractive index adhesive such as, for example, an acrylate which has a refractive index of approximately 1.3. In one configuration, an adhesive can be for example a high refractive index adhesive which includes for example high refractive index, non-scattering particles and has a mean refractive index corresponding approximately to the mean refractive index of the organic functional layer structure, for example in a range of approximately 1.7 to approximately 2.0. Furthermore, a plurality of different adhesives can be provided, which form an adhesive layer sequence.

Furthermore, it should be pointed out that, in various embodiments, an adhesive 124 can also be completely dispensed with, for example in configurations in which the cover 126, for example composed of glass, is applied to the barrier thin-film layer 108 by plasma spraying, for example.

In various embodiments, the cover 126 and/or the adhesive 124 can have a refractive index (for example at a wavelength of 633 nm) of 1.55.

Furthermore, in various embodiments, one or a plurality of antireflective layers (for example combined with the encapsulation 108, for example the barrier thin-film layer 108) can additionally be provided in the light emitting component 100.

Figure 2:
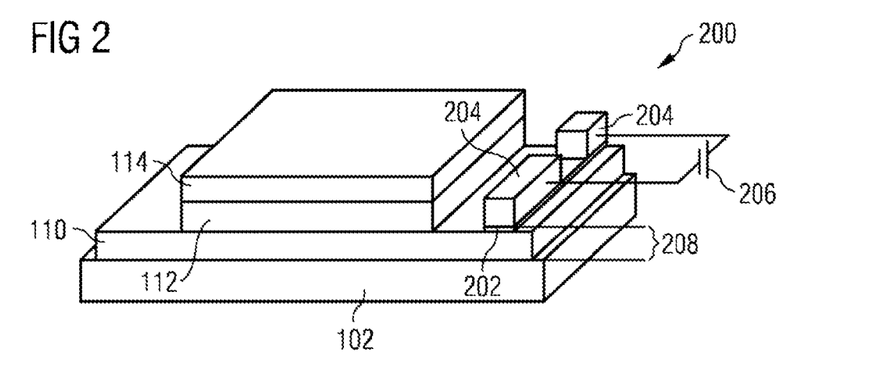
FIG. 2 shows a schematic view of an optoelectronic component, in accordance with various configurations.

FIG. 2 shows a schematic view of an optoelectronic component, in accordance with various configurations.

FIG. 2 illustrates a configuration for working an apparatus including an electrical layer structure 208 on the basis of the example of the first electrode 110 of an optoelectronic component 100. The optoelectronic component illustrated can correspond for example to a configuration from the description of FIG. 1.

On or above the first electrode 110, a plurality of electrical contacts 204, electrically insulated from one another, can be formed or arranged, for example arranged in a manner spatially separated from one another.

The electrical contacts 204 on or above the the first electrode 110 can be designed to be temporary or permanent.

An electrical contact 204 designed to be temporary can be designed for example as a contact pin, pin, or the like.

An electrical contact 204 designed to be permanent can be formed for example as a contact pad 204 on or above the first electrode 110, for example can be deposited or applied thereon and/or can be closely connected to the first electrode 110, for example adhesively bonded, soldered, screwed, riveted or the like.

The contact pads 204 can be designed for example for electrical connection of the first electrode 110.

The contact pads 204 can be embodied for example materially identically to one of the configurations of the first electrode 110 and/or the second electrode 114, for example may include or be formed from molybdenum, silver, copper, gold, titanium, chromium and/or aluminum.

The first electrode 110 and/or the electrical contacts 204 can for example oxidize; for example, the first electrode 110 can oxidize before the formation of the contact pad 204 on or above the first electrode 110. As a result, for example, a native, dielectric oxide layer 202 can form at the surface of the first electrode 110. As a result, the physical contact of the first electrode 110 with the contact pad 204 after the formation of the contact pad 204 may include a dielectric oxide layer 202.

In this configuration, the dielectric oxide layer 202 and the first electrode 110 can be understood as an electrical layer structure 208.

When an electrical connection is formed between the contact pad 204 and the first electrode 110, for example by the electrical contact pads 204 being connected to a voltage source 206, a voltage can be dropped across the dielectric oxide layer 202, i.e. the dielectric oxide layer 202 can act as an electrical resistor.

The voltage source 206 can generate a temporally modulated voltage profile, for example. The temporally modulated voltage profile can have voltage pulses, for example.

The voltage pulses can be designed for example in such a way that the breakdown strength of the oxide layer 202 can be exceeded, as a result of which electrically conductive contact paths can be formed in the physical contact of the contact pad 204 with the first electrode 110. As a result, the electrical layer structure 208 can become electrically conductive. In other words, the electrical conductivity of the electrical layer structure can increase as a result.

In other words: the voltage drop across the dielectric oxide layer 202 can be reduced by the contacting of the electrical layer structure 208 and the electrical breakdown of the dielectric oxide layer 202.

The breakdown of the oxide layer 202 by voltage pulses can also be designated as release by pulsing.

Assuming a linear dependence of the breakdown strength on the layer thickness and an oxide layer 202 having a thickness of a few nanometers, even in the case of oxides having a high breakdown strength, an electrical breakdown of the oxide layer 202 can be effected when an electrical voltage of a few volts is applied.

An oxide having a high breakdown strength can be aluminum oxide ($Al_2O_3$), for example, having a breakdown strength of approximately 35 kV/mm.

In one configuration, the voltage pulses can have for example a maximum voltage value, for example a peak voltage, of greater than approximately 1 V, for example in a range of approximately 5 V to approximately 100 V, for example in a range of approximately 10 V to approximately 60 V.

In one configuration, the contact pad 204 can have an oxide layer (not illustrated) which is intended to be released by pulsing, for example by temporary contacts.

In one configuration, the apparatus can have a steady-state contact 204 and a temporary contact 204.

In one configuration, the apparatus can have a plurality of electrical contacts 204 (illustrated: two), such that the dielectric oxide layer 202 of the first electrode can be released by pulsing, without further layers of the optoelectronic component 100 being energized.

In a further configuration, for example, the contact resistance of the interface of the second electrode 114 can be reduced in a manner similar or identical to the first electrode 110 by the method described above.

As a result, for example, the electrical resistance of the dielectric surface of the electrodes 110, 114 can be reduced for example from a magnitude in a range of approximately 5Ω to approximately 100Ω to a magnitude of less than approximately 0.5Ω (see, for example, description of FIGS. 5A-5B, FIGS. 6A-B and FIGS. 7A-7B), for example can have a contact resistance of approximately 0Ω, for example no measurable contact resistance.

In one configuration, when forming an optoelectronic component in accordance with one of the configurations from the description of FIG. 1, the contacting and the electrical breakdown of the dielectric oxide layer 202 can be effected before the encapsulation 108 is formed.

Figure 3:
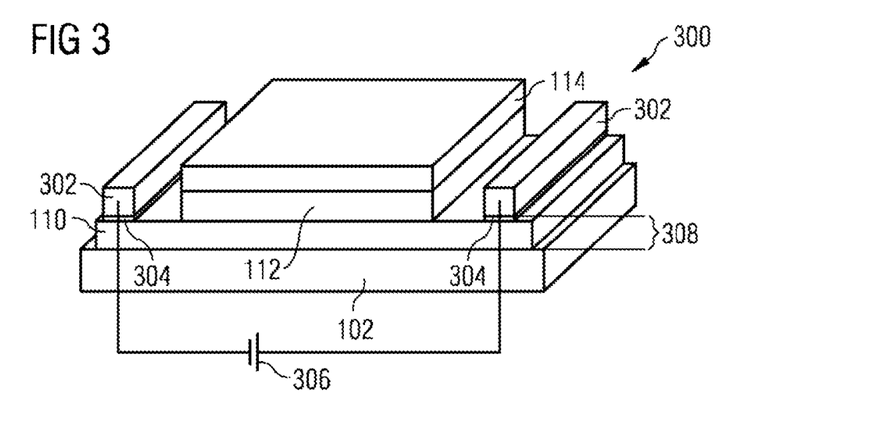
FIG. 3 shows a schematic view of an optoelectronic component, in accordance with various configurations.

FIG. 3 shows a schematic view of an optoelectronic component, in accordance with various configurations.

The illustration shows a view of an optoelectronic component similar to one of the configurations from the description of FIG. 1 and/or FIG. 2.

The electrical contacts 302 (204) and/or the dielectric oxide layer 304 (202) can be designed in a manner similar or identical to one of the configurations from the description of FIG. 2.

In one configuration, it is possible to form an electrically conductive layer 110 with an electrically insulating surface 304, for example with a dielectric oxide layer 304, for example the first electrode 110 with a native oxide layer 304, with a plurality of contacts 302 and/or a contact strip 304—illustrated in view 300.

An interrupted contact strip can be understood as contacts spatially separated from one another, for example in accordance with one of the configurations from the description of FIG. 2.

By the plurality of contacts 302, an electrical potential can be applied to the dielectric oxide layer 304.

In a further configuration, for example, electrical contact can be made through the dielectric oxide layer (not illustrated) of the second electrode 114 in a manner similar to the dielectric oxide layer 304 of the first electrode 110 by electrical contacts 302 and a temporally modulated electrical voltage profile of the voltage source 306.

Figure 4:
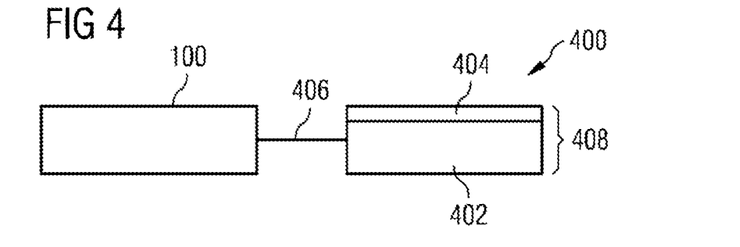
FIG. 4 shows a schematic view of an optoelectronic component, in accordance with various configurations.

FIG. 4 shows a schematic view of an optoelectronic component, in accordance with various configurations.

The apparatus may include an electrical layer structure 408, having an electrically conductive layer 402 and a dielectric layer 404, such as is electrically connected to an electronic component by an electrical connection 406, for example to an optoelectronic component 100 in accordance with one of the configurations in FIG. 1.

The electrical layer structure 408 can be designed or formed for example as a busbar 408 for electrical contact of the electronic component 100.

In other words: the apparatus may include an electrical layer structure 408 arranged alongside an electronic component.

Figure 5A:
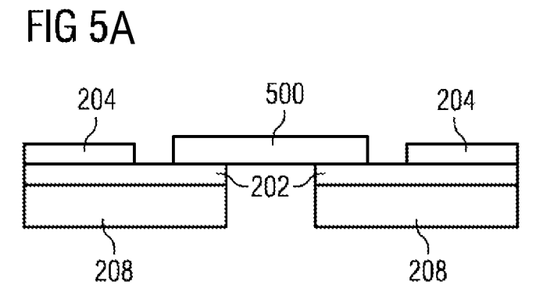
FIGS. 5A and 5B show illustrations for working an apparatus, in accordance with various configurations.
Figure 5B:
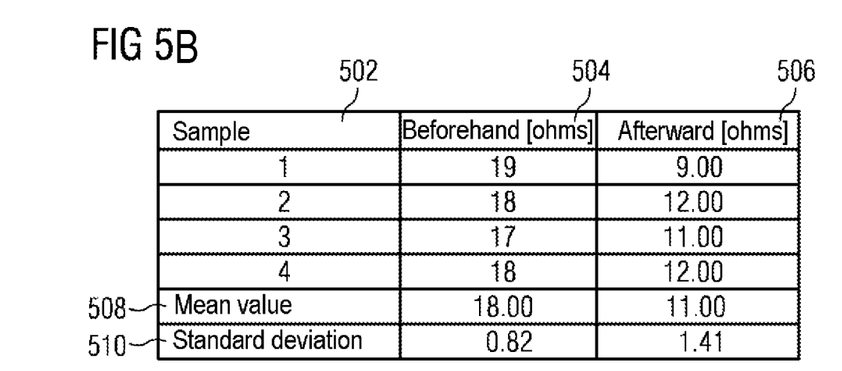

FIGS. 5A and 5B show an illustration for working an apparatus, in accordance with various configurations.

FIG. 5A shows a schematic cross-sectional view of an excerpt from a component arrangement in the method for working an apparatus, for example an optoelectronic component in accordance with one of the configurations from the description of FIG. 1 to FIG. 4.

The illustration shows an electrical layer structure 208 which is electrically contacted with two electrical contacts 204. The two electrical layer structures 208 are electrically connected to one another by an electrical connection structure 500.

The electrical layer structures 208 are formed as chromium-aluminum-chromium layer stacks, for example as a metal contact 208 of an optoelectronic component in accordance with a configuration from the description of FIG. 1 to FIG. 4. The electrical contacts 204 are formed as contact pins. The electrical connection structure 500 includes magnesium and silver.

The surface of the electrical layer structure 208, for example of the chromium surface, can have a native oxide layer 202 before the electrical connection structure 500 is formed. This oxide layer 202 can lead to a contact resistance.

By the electrical contacts 204, through the electrical connection structure 500 there is passed at least one electrical voltage pulse having an amplitude of 10 V and a 10 mA conforming current (compliance) which leads to a reduction of the contact resistance of the component arrangement.

FIG. 5B shows an overview of the contact resistance 504, 506 of a number 502 of component arrangements.

The illustration shows the contact resistance before the application of the voltage pulses 504 and after the through-contacting 506 for four component arrangements in accordance with the description of FIG. 5A.

The mean value 508 and the standard deviation 510 of the contact resistances 504, 506 are furthermore illustrated.

Figure 6A:
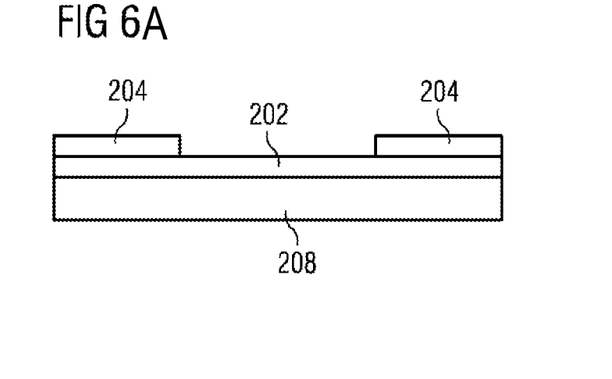
FIGS. 6A and 6B show illustrations for working an apparatus, in accordance with various configurations.
Figure 6B:
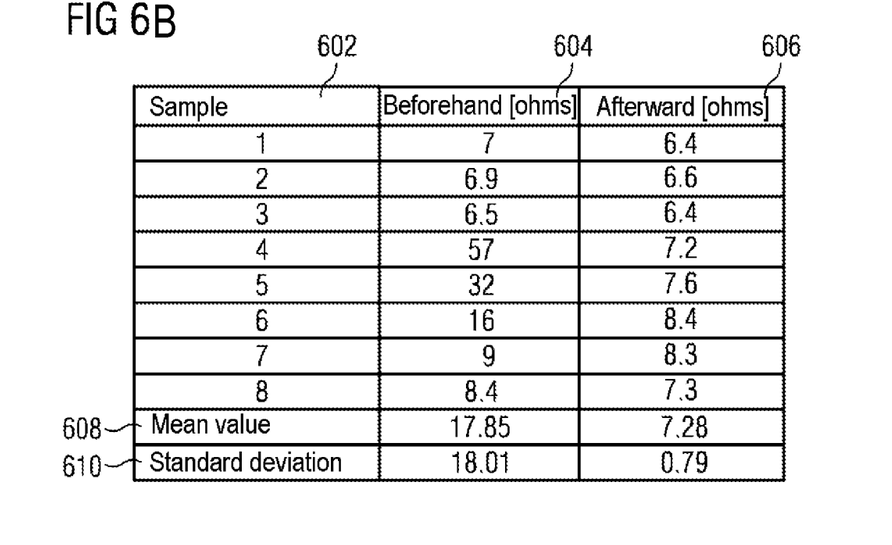

FIGS. 6A and 6B show an illustration for working an apparatus, in accordance with various configurations.

FIG. 6A shows a schematic cross-sectional view of an excerpt from a component arrangement in the method for working an apparatus, for example an optoelectronic component, in accordance with one of the configurations from the description of FIG. 1 to FIG. 4.

The illustration shows an electrical layer structure 208 which is electrically contacted with two electrical contacts 204.

The electrical layer structures 208 is formed as a chromium-aluminum-chromium layer stack, for example as a contact track 208 of an optoelectronic component in accordance with a configuration from the description of FIG. 1 to FIG. 4. The electrical contact 204 is formed as a silver paste.

The surface of the electrical layer structure 208, for example of the chromium surface, can have an oxide layer 202, for example in a manner similar to the barrier thin-film layer 108 from the description of FIG. 1, and/or a native oxide layer.

Before the electrical contact 204 is formed, a part of the oxide layer is removed ballistically. The remainder of the oxide layer 202 can lead to a contact resistance—see 604 in FIG. 6B.

There are passed through the electrical layer structure 208 voltage pulses having an amplitude of 20 V and a 50 mA conforming current (compliance) which leads to a reduction of the contact resistance of the component arrangement.

FIG. 6B shows an overview of the contact resistance 604, 606 of a number 602 of component arrangements.

The illustration shows the contact resistance before the application of the voltage pulses 604 and after the through-contacting 606 for eight component arrangements in accordance with the description of FIG. 6A.

The mean value 608 and the standard deviation 610 of the contact resistances 604, 606 are furthermore illustrated.

Figure 7A:
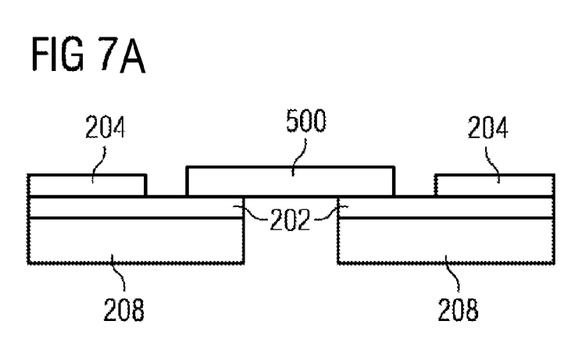
FIGS. 7A and 7B show illustrations for working an apparatus, in accordance with various configurations.
Figure 7B:
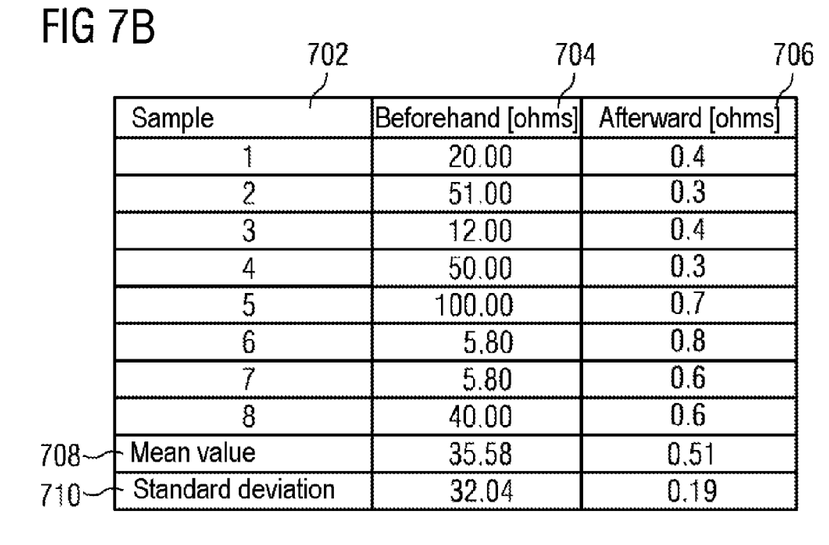

FIGS. 7A and 7B show an illustration for working an apparatus, in accordance with various configurations.

FIG. 7A shows a schematic cross-sectional view of an excerpt from a component arrangement in the method for working an apparatus, for example an optoelectronic component in accordance with one of the configurations from the description of FIG. 1 to FIG. 4.

The illustration shows two electrical layer structures 208 which are electrically contacted with two electrical contacts 204 and are connected to one another by an electrical connection structure 500.

The electrical layer structures 208 is formed as chromium-aluminum-chromium layer stacks, for example as a contact track 208 of an optoelectronic component in accordance with a configuration from the description of FIG. 1 to FIG. 4. The electrical contacts 204 are formed as silver paste. The electrical connection structure 500 is formed as a silver contact track 500.

The surface of the electrical layer structure 208, for example of the chromium surface, can have an oxide layer 202, for example in a manner similar to the barrier thin-film layer 108 from the description of FIG. 1 and/or a native oxide layer.

Before the electrical contact 204 and/or the electrical connection structure 500 are/is formed, a part of the oxide layer can be removed ballistically. The remainder of the oxide layer 202 can lead to a contact resistance—see 704 in FIG. 7B.

By the electrical contacts 204, there is passed through the electrical connection structure 500 at least one electrical voltage pulse having an amplitude of 20 V and a 50 mA conforming current (compliance) which leads to a reduction of the contact resistance of the component arrangement.

FIG. 7B shows an overview of the contact resistance 704, 706 of a number 702 of component arrangements.

The illustration shows the contact resistance before the application of the voltage pulses 704 and after the through-contacting 706 for eight component arrangements in accordance with the description of FIG. 6A.

The mean value 708 and the standard deviation 710 of the contact resistances 704, 706 are furthermore illustrated.

In various embodiments, a method for working an apparatus having at least one electrical layer structure and a component arrangement for working an apparatus having at least one electrical layer structure are provided which make it possible, by an adapted construction of the optoelectronic component, to handle process-dictated contact resistances of electrically conductive layers with voltage pulses, such that the electrical resistance of the electrically conductive layer can be greatly reduced. Consequently, alternative processes, for example printing the electrically conductive layer, and/or simplified process conditions, for example producing the electrically conductive layers in air, can be realized without disadvantages for the component parts treated.

While the disclosed embodiments have been particularly shown and described with reference to specific embodiments, it should be understood by those skilled in the art that various changes in form and detail may be made therein without departing from the spirit and scope of the disclosed embodiments as defined by the appended claims. The scope of the disclosed embodiments is thus indicated by the appended claims and all changes which come within the meaning and range of equivalency of the claims are therefore intended to be embraced.

The invention claimed is:

1. A method for working an apparatus having at least one electrical layer structure, wherein the electrical layer structure comprises a dielectric layer in physical contact with an electrically conductive layer and the electrical layer structure has a first electrical conductivity, the method comprising:
    forming an electrical connection to the dielectric layer of the electrical layer structure;
    forming an electrical voltage profile at the electrical connection in such a way that a second electrical conductivity is formed; wherein the second electrical conductivity is greater than the first electrical conductivity; and
    reducing the electrical voltage profile at the electrical connection, wherein the electrical layer structure has the second electrical conductivity after the reduction of the electrical voltage profile,
    wherein in at least one region of the electrical layer structure a part of the dielectric layer of the electrical layer structure is removed before the electrical connection is formed.

2. The method as claimed in claim 1,
    wherein the dielectric layer includes a substance or a substance mixture, wherein the applied electrical voltage profile has a maximum magnitude of the voltage which is greater than the breakdown voltage of the substance or of the substance mixture of the dielectric layer.

3. The method as claimed in claim 1,
    wherein the apparatus comprises an electronic component unit, wherein the electrical layer structure is formed as a region of the electronic component unit or is electrically connected to a region of the electronic component unit.

4. The method as claimed in claim 3,
    wherein the electrically conductive layer of the electrical layer structure is designed as an electrical bus which is electrically connected to the electronic component unit.

5. The method as claimed in claim 3,
    wherein the electrically conductive layer of the electrical layer structure is designed as an electrode or a contact pad of the electronic component unit.

6. The method as claimed in claim 1,
    wherein the dielectric layer of the electrical layer structure is designed as a thin-film encapsulation and/or comprises a dielectric metal oxide.

7. The method as claimed in claim 1,
    wherein the magnitude of the voltage of the electrical voltage profile is temporally modulated.

8. The method as claimed in claim 7,
    wherein the maximum magnitude of the electrical voltage profile has a magnitude of greater than approximately 1 V.

9. The method as claimed in claim 1,
    wherein removing a part of the dielectric layer comprises ballistically removing the dielectric layer.

10. The method as claimed in claim 1,
    wherein the electrical connection to the electrical layer structure is formed in the region of the removed dielectric layer.

11. The method as claimed in claim 1,
    wherein the dielectric layer is at least partly removed from at least two regions of the electrical layer structure.

12. The method as claimed in claim 1,
    wherein the apparatus is formed as a component which provides electromagnetic radiation; or
    wherein the apparatus is formed as a component which takes up electromagnetic radiation.

13. A component arrangement for working an apparatus having at least one electrical layer structure having a first electrical conductivity, the component arrangement comprising:
    an apparatus having at least one electrical layer structure, wherein the electrical layer structure comprises a dielectric layer in physical contact with an electrically conductive layer and the electrical layer structure has a first electrical conductivity, and wherein in at least one region of the electrical layer structure a part of the dielectric layer of the electrical layer structure is removed;
    a voltage source designed for providing a modulatable voltage profile, wherein the voltage source is electrically connected to the electrical layer structure in such a way that the electrical circuit is closed by the electrical layer structure and that the electrical connection with the electrical layer structure is formed in the region of the removed dielectric layer;
    a control unit designed for controlling the voltage profile of the voltage source; and
    a measuring device for measuring the electrical conductivity of the electrical layer structure, wherein the measuring device is designed in such a way that the measured electrical conductivity is communicated to the control unit;
    wherein the control unit is designed in such a way that the voltage profile is controlled depending on the measured electrical conductivity.

14. The component arrangement as claimed in claim 13, wherein the measuring device is designed for measuring the electrical resistance of the electrical layer structure.

15. The component arrangement as claimed in claim 13, wherein the measuring device is designed for measuring the electrical voltage drop across the electrical layer structure.

16. The component arrangement as claimed in claim 13, wherein the measuring device is designed for measuring the electric current through the electrical layer structure.

17. The component arrangement as claimed in claim 13, wherein the control unit is designed as a phase dimmer, wherein the control signal for phase chopping control or phase gating control is a function of the measured conductivity.

18. The component arrangement as claimed claim 13, wherein the control unit is designed as a pulse modulator, wherein the control signal for pulse modulation is a function of the measured conductivity.

* * * * *